United States Patent [19]

Bottom et al.

[11] Patent Number: 5,010,069

[45] Date of Patent: Apr. 23, 1991

[54] STABLE LIQUID FORM OF 5-AMINOSALICYLIC ACID

[75] Inventors: Carey B. Bottom, Overland Park; Margaret N. Kwoka, Merriam, both of Kans.

[73] Assignee: Marion Laboratories, Inc., Kansas City, Mo.

[21] Appl. No.: 352,064

[22] Filed: May 15, 1989

[51] Int. Cl.$^5$ .................... A61K 31/615; A61K 31/34
[52] U.S. Cl. ..................... 514/166; 514/474; 514/973
[58] Field of Search .............. 514/166, 474, 973

[56] References Cited

U.S. PATENT DOCUMENTS 2,647,853  8/1953  Larde et al. ............. 514/973
4,657,900  4/1987  Powell et al. ............ 514/166
4,664,256  5/1987  Halskov .................. 514/166

Primary Examiner—Thurman K. Page
Assistant Examiner—G. S. Kishore
Attorney, Agent, or Firm—Quarles & Brady

[57] ABSTRACT

An aqueous solution of 5-aminosalicylic acid (5-ASA) and a nontoxic alkali, alkali metal or alkaline earth metal salt of 5-aminosalicylic acid having a pH of 3-5 is disclosed. The sole buffer in the solution is that intrinsically formed by 5-aminosalicylic acid and its alkali, alkali metal or alkaline earth metal salt. The solutions preferably also contain an antioxidant and a metal complexing agent. In preferrred practice, the 5-ASA salt is formed in situ by addition of an alkali, alkali metal or alkaline earth metal hydroxide to a solution of 5-ASA. The solution is stable and does not significantly discolor due to 5-ASA decomposition for extended periods of time.

17 Claims, No Drawings

STABLE LIQUID FORM OF 5-AMINOSALICYLIC ACID

BACKGROUND OF THE INVENTION (a) Field of the Invention

This invention relates to a stable 5-aminosalicylic acid solution or suspension.

(b) State of the Art

5-Aminosalicylic acid (5-ASA) is a known compound having utility in the treatment of various conditions of the gastrointestinal tract including Crohn's disease and ulcerative colitis. Where the disorder site is in the lower gastrointestinal tact, administration of the compound in a liquid enema is in some cases the preferred mode. In other cases, a patient may be more readily treated by an oral liquid form rather than with solid formulations.

To date, use of 5-ASA in liquid form has not been entirely satisfactory. 5-ASA is currently formulated in buffered solutions with a combination of 5-ASA, a buffer e.g. citrate or acetate, an antioxidant e.g. metabisulfite, and a chelating agent e.g. ethylenediamine-tetraacetic acid (EDTA). In such formulations, 5-ASA acid decomposes and the liquid takes on an unsightly muddy brownish appearance after only short storage periods. During manufacturing, an inert atmosphere must be maintained or a yellowing of the solution will occur. Extreme care must be taken in processing the enema bottles as large muddy brown deposits occur on the bottles wherever 5-ASA residues remain. Even trace amounts of 5-ASA result in an extremely unsightly product. Further, the decomposed 5-ASA stains materials with which it comes into contact.

In U.S. Pat. No. 4,664,256 a packaged enema solution of 5-ASA is described which includes a citric acid buffer to maintain the pH at a value of 4.8. A similar packaged 5-ASA enema product is described in U.S. Pat. No. 4,657,900, wherein potassium acetate is disclosed as a buffer. This particular patent is concerned with the use of bisulfite to stabilize the solution against discoloration.

Recently, it has been discovered that sodium phosphate in an enema solution can be fatal if employed at high concentrations. This is reported in JAMA, Apr. 24, 1987, Vol 257, No. 16, pages 2190–92. Sodium or potassium phosphate is commonly used as an extrinsic buffer in pharmaceutical preparations.

Unexpectedly, it has been discovered that avoidance of extrinsic buffers such as citrates, phosphates and acetates greatly enhances the stability of 5-ASA liquid formulations.

SUMMARY OF THE INVENTION

This invention comprises 5-ASA in a liquid form, such as a solution or suspension. The composition of the invention is an aqueous solution of 0.5 to 4 g/100 ml of 5-ASA, and a soluble alkali, alkali metal or alkaline earth metal salt of 5-ASA preferably formed by adding sufficient alkali or alkali metal hydroxide to the aqueous solution to raise the pH to 3 to 5. As used herein the term "alkali metal" is meant to include the alkaline earth metals. Optimally, the solution also contains an antioxidant and/or an agent for complexing metal ions. The solution contains no buffer other than that intrinsically formed by 5-ASA and its salts. The composition is stable for extended periods of time with little more than a slight yellowing of the solution.

DETAILED DESCRIPTION OF THE INVENTION

The essence of the present invention is the discovery that the elimination of extrinsic buffers from aqueous 5-ASA solutions greatly retards the decomposition and ensuing discoloration of 5-ASA. By extrinsic buffers, is meant buffering agents other than that which are intrinsically formed when 5-ASA and its nontoxic alkali, or alkali metal salts are both present in solution. As 5-ASA is amphoteric, the combination of 5-ASA and such salts produces an intrinsic buffer.

More specifically, the present invention provides solutions or suspensions (herein collectively termed solutions) of 5-ASA which are stable for extended periods of time. The solutions contain no extrinsic buffers but rather rely solely upon the intrinsic buffer which exists when 5ASA and its nontoxic alkali, alkali metal or alkaline earth metal salts are combined. The sodium salt of 5-ASA is preferred for purposes of the invention but the $K^+$, $NH_4^+$, and $Ca^{++}$ salts may also be used.

The solutions are useful for purposes of administering 5-ASA to patients having conditions within the gastrointestinal tract for which 5-ASA is therapeutic. The solutions of the invention contain sufficient free 5-ASA and its salts to produce the desired therapeutic effect, with dosing amounts and intervals being in accordance with those known or taught in the art. The mode of administration may be oral, by nasal tube or by enema depending upon the desired therapeutic effect and the condition of the patient.

Preferably, the solutions are formulated by suspending 5-ASA in water to create a final dilution of 0.5 to 4 g/100 ml. If desired, a concentration of about 0.1–10 g/100 ml is used. The solutions have a pH of 3 to 5, preferably 4. The desired pH may initially be produced by means of an alkali metal hydroxide such as sodium hydroxide which also forms sodium-5-amino salicylate, a component of the intrinsic buffer with 5-ASA. A ratio range of 10:1 to 500:1 of 5-ASA to Na-5-ASA is preferred.

The solutions may contain additional components such as antioxidants and metal complexing agents. Among suitable antioxidants are metabisulfite and ascorbic acid with both preferred over butylated hydroxytoluene. When used, the antioxidant will commonly be present in amounts of 0.05 to 0.5 g/100 ml. EDTA is an example of a suitable metal chelating agent. The metal chelating agent may commonly be present in amounts ranging from 0.01 to 0.1 g/100 ml.

In preferred practice the compositions of the invention are formulated by combining 5-ASA, the antioxidant and the metal chelating agent, adding water to provide the desired concentration and then forming the alkali or alkali metal salts of 5-ASA by adding sufficient alkali or alkali metal hydroxide to raise the pH to the desired level. An inert atmosphere is employed to avoid decomposition during formulation.

In a most preferred practice the solution of the invention for use as an enema has the following ingredients and amounts:

| Ingredient | g/100 ml |
| --- | --- |
| 5-ASA and Na-5-amino-salicylate | 1.000 (formed in situ by addition of NaOH to pH4.) |
| EDTA, disodium | 0.020 |

| Ingredient | g/100 ml |
| --- | --- |
| Metabisulfite | 0.100 |
| Purified Water | q.s. |

The solutions of the invention may be packaged according to techniques used for other products intended for similar use. (e.g. in enema bottles for enema applications). They would be filled into the enema bottles under an inert atmosphere using standard form, fill and seal procedures.

The following examples are illustrative of the invention and are set forth for the purpose of illustrating the present invention. They should not be construed to limit the invention to the precise ingredients, proportions or other conditions specified.

EXAMPLE 1

Stabilized 5-ASA and Sodium Metabisulfite

| Materials | Amount |
| --- | --- |
| Sodium Hydroxide (1M) | 225 ml |
| Sodium Metabisulfite | 300 gm |
| Sodium EDTA | 60 gm |
| 5-ASA | 3,000 gm |
| Nitrogen Gas | (To Purge) |
| Purified Water | 200L, q.s. 300L |

200 liters of the purified water are added to a suitable mixing tank which is purged with nitrogen gas. The sodium hydroxide, sodium metabisulfite and sodium EDTA are then added to the water and mixed until dissolved. To this mixture is admixed the 5-ASA and the mixing continued until uniform. A check of the pH is made and adjusted to 4.0 with sodium hydroxide if necessary. Additional water is added to the solution so as to q.s. to 300L.

The resulting stabilized 5-ASA product is filled into enema bottles under a nitrogen atmosphere at the rate of 100 ml/bottle. A Bottle Pack machine was used which includes bottle moulding, suspension filling and bottle sealing.

EXAMPLE 2

Stabilized 5-ASA and Ascorbic Acid

The same materials as described in Example 1 were employed except that 300 gm of ascorbic acid were substituted for 300 gm of sodium metabisulfite. The same mixing procedures and conditions were also employed as well as the same filling step to result in a packaged stabilized 5-ASA product.

In the preceeding Examples, the Na-5-amino salicylate intrinsic buffer was prepared with an alkali metal hydroxide such as sodium hydroxide and 5-ASA. The corresponding potassium alkali metal, alkali ammonium salt or calcium alkaline earth metal salt can also be produced by substituting, respectively, potassium, ammonium or calcium hydroxide for the sodium hydroxide according to the previously indicated procedures and conditions. Obviously, other nontoxic alkali metal salts employing metals of Group IA of the Periodic Table of Elements and nontoxic salts of alkaline earth metals of Group IIA of the Periodic Table could be produced and utilized in a similar manner.

The following Tables 1 & 2 illustrate the comparative stability of an extrinsically buffered 5-ASA composition (Table 1) and the intrinsically buffered 5-ASA composition of this invention (Table 2). The buffer employed in the studies shown in Table 1 was sodium acetate while that employed in Table 2 was the Na-5-amino salicylate. In the instance of Table 1, the color observations were made after 69 days, whereas with respect to Table 2, the observations were made after 68 days.

TABLE 1

| Additives | Air | Nitrogen | Carbon Dioxide |
| --- | --- | --- | --- |
| None | Dark Brown/ Purple | Light Brown Brown Dark Brown | Brown Dark Brown Dark Brown |
| Sodium Metabisulfite | Brown | Dark Orange Dark Orange Dark Orange | White/Off-White Orange |
| Ascorbic Acid | Dark Brown | Dark Brown Dark Brown Dark Brown | Off-White/Pale Yellow Yellow Light Brown |
| EDTA | Dark Brown | Dark Brown Dark Brown Dark Brown | Brown Brown Brown |
| Sodium Metabisulfite and EDTA | Brown | Dark Orange Dark Orange Dark Orange | Yellow/Orange Orange Orange |
| Ascorbic Acid and EDTA | Dark Brown | Dark Brown Dark Brown Dark Brown | Dark Orange/ Brown Dark Orange/ Brown Dark Brown |

TABLE 2

| Additives | Air | Nitrogen | Carbon Dioxide |
| --- | --- | --- | --- |
| None | Dark Brown/ Purple | Light Brown Light Brown Dark Brown | Brown Brown Dark Brown |
| Sodium Metabisulfite | Orange | Off-White Off-White Off-White | Off-White Pale Yellow Yellow |
| Ascorbic Acid | Dark Brown | Off-White Off-White Off-White | Off-White Pale Yellow Brown |
| EDTA | Dark Brown | Beige/Pink Beige/Pink Beige/Pink | Beige/Light Brown Brown Brown |
| Sodium Metabisulfite and EDTA | Orange | Off-White Yellow Yellow | Yellow Yellow Yellow |
| Ascorbic Acid and EDTA | Dark Brown | Off-White/ Light Yellow Dark Brown Dark Brown | Beige/Light Yellow Yellow Dark Brown |

It will be appreciated that in conjunction with those studies using nitrogen and carbon dioxide as blanketing agents that in most instances 3 separate samples were made and in some instances 4 were made. This is indicated by the reported observations. Best results were obtained when using the intrinsic buffer of this invention in conjunction with sodium metabisulfite and ascorbic acid with the nitrogen cover.

The foregoing invention can now be practiced by those skilled in the art. Such skilled persons will know that the invention is not necessarily restricted to the particular embodiments presented therein. The scope of the invention is to be defined by the terms of the following claims as given meaning by the preceding description.

We claim:

1. A stabilized aqueous solution having a concentration of 0.1 to 10 g/100 ml of 5-aminosalicylic acid wherein a buffer consists essentially of an intrinsic, water soluble nontoxic alkali, alkali metal or alkaline earth metal salt of 5-aminosalicylic acid, said solution having a pH of 3 to 5.

2. The solution of claim 1 further including an antioxidant.

3. The solution of claim 2 wherein the antioxidant is metabisulfite.

4. The solution of claim 2 wherein the antioxidant is ascorbic acid.

5. The solution of claim 1 further including EDTA or the disodium salt thereof.

6. The solution of claim 1 wherein the alkali or alkali metal salt of 5-aminosalicylic acid has been formed in situ by addition of an alkali metal, alkaline earth metal or alkali hydroxide to an aqueous solution of 5-aminosalicylic acid.

7. The solution of claim 1 wherein the alkali metal salt is sodium.

8. The solution of claim 1 wherein the alkali metal salt is potassium.

9. The solution of claim 1 wherein the alkali salt is ammonium.

10. The solution of claim 1 wherein the alkaline earth metal salt is calcium.

11. The solution of claim 1 wherein the ratio of 5-aminosalicylic acid to sodium 5-aminosalicylic acid is in the range of 10:1 to 500:1.

12. The solution of claim 1 comprising: 0.5 to 4 g/100 ml 5-amino salicylic acid and sodium 5-aminosalicylate; 0.05 to 0.5 g/100 ml sodium metabisulfite and 0.01 to 0.1 g/100 ml EDTA.

13. The use of the composition of claim 1 as an enema product.

14. A stabilized aqueous solution of 5-aminosalicylic acid having a pH of about 4 in which the sole buffer consists essentially of a nontoxic alkali, or alkali metal or alkaline earth metal salt of 5-aminosalicylic acid in the solution.

15. The solution of claim 14 wherein the alkali metal salt of 5-aminosalicylic acid has been formed by addition of an alkali metal hydroxide to an aqueous solution of 5-aminosalicylic acid.

16. The solution of claim 14 wherein the alkali salt of 5-aminosalicylic acid has been formed by addition of ammonium hydroxide to an aqueous solution of 5-aminosalicylic acid.

17. The solution of claim 14 wherein the alkaline earth metal salt of 5-aminosalicylic acid has been formed by addition of calcium hydroxide to an aqueous solution of 5-aminosalicylic acid.

* * * * *